(12) United States Patent
Jarrouj

(10) Patent No.: US 9,622,999 B2
(45) Date of Patent: Apr. 18, 2017

(54) COMPOSITION AND METHOD FOR INCREASING THE RATE OF ALCOHOL METABOLISM AND PREVENTING HANGOVER SYMPTOMS

(71) Applicant: Salim Jarrouj, Windsor (CA)

(72) Inventor: Salim Jarrouj, Windsor (CA)

(*) Notice: Subject to any disclaimer, the term of this patent is extended or adjusted under 35 U.S.C. 154(b) by 0 days.

(21) Appl. No.: 15/033,721

(22) PCT Filed: Nov. 6, 2014

(86) PCT No.: PCT/CA2014/000807
§ 371 (c)(1),
(2) Date: May 2, 2016

(87) PCT Pub. No.: WO2015/066799
PCT Pub. Date: May 14, 2015

(65) Prior Publication Data
US 2016/0256423 A1    Sep. 8, 2016

Related U.S. Application Data

(60) Provisional application No. 61/900,429, filed on Nov. 6, 2013.

(51) Int. Cl.

| | | |
|---|---|---|
| *A61K 31/198* | (2006.01) |
| *A61K 31/714* | (2006.01) |
| *A61K 33/14* | (2006.01) |
| *A61K 31/047* | (2006.01) |
| *A61K 31/14* | (2006.01) |
| *A61K 31/197* | (2006.01) |
| *A61K 31/375* | (2006.01) |
| *A61K 31/4188* | (2006.01) |
| *A61K 31/4415* | (2006.01) |
| *A61K 31/455* | (2006.01) |
| *A61K 31/51* | (2006.01) |
| *A61K 31/519* | (2006.01) |
| *A61K 31/525* | (2006.01) |
| *A61K 33/06* | (2006.01) |
| *A61K 33/26* | (2006.01) |
| *A61K 33/30* | (2006.01) |
| *A61K 33/42* | (2006.01) |
| *A61K 36/258* | (2006.01) |
| *A61K 31/593* | (2006.01) |
| *A61K 33/20* | (2006.01) |
| *A61K 33/32* | (2006.01) |
| *A61K 31/196* | (2006.01) |
| *A61K 31/4406* | (2006.01) |
| *A61K 31/555* | (2006.01) |
| *A61K 31/59* | (2006.01) |
| *A61K 33/00* | (2006.01) |

(52) U.S. Cl.
CPC .......... *A61K 31/198* (2013.01); *A61K 31/047* (2013.01); *A61K 31/14* (2013.01); *A61K 31/196* (2013.01); *A61K 31/197* (2013.01); *A61K 31/375* (2013.01); *A61K 31/4188* (2013.01); *A61K 31/4406* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/555* (2013.01); *A61K 31/59* (2013.01); *A61K 31/593* (2013.01); *A61K 31/714* (2013.01); *A61K 33/00* (2013.01); *A61K 33/06* (2013.01); *A61K 33/14* (2013.01); *A61K 33/20* (2013.01); *A61K 33/26* (2013.01); *A61K 33/30* (2013.01); *A61K 33/32* (2013.01); *A61K 33/42* (2013.01); *A61K 36/258* (2013.01)

(58) Field of Classification Search
None
See application file for complete search history.

(56) References Cited

U.S. PATENT DOCUMENTS

| | | | | |
|---|---|---|---|---|
| 6,967,031 B1* | 11/2005 | Oslick | ............... | A23L 33/165 424/638 |
| 7,449,448 B2* | 11/2008 | McGregor | ......... | A61K 31/7004 514/23 |
| 8,137,712 B2 | 3/2012 | Hays | | |
| 8,440,242 B1 | 5/2013 | Grady | | |
| 2005/0238710 A1* | 10/2005 | Connolly | ............... | A61K 31/14 424/464 |
| 2007/0286909 A1* | 12/2007 | Smith | ................. | A61K 31/198 424/682 |
| 2013/0017276 A1* | 1/2013 | Blackman | ............ | A61K 31/133 424/717 |

FOREIGN PATENT DOCUMENTS

| | | | | |
|---|---|---|---|---|
| CN | 101766636 B | 11/2012 | | |
| DE | WO 2012120036 A1 * | 9/2012 | ............ | A23L 1/302 |
| EP | 1743634 A1 | 1/2007 | | |
| EP | 1757289 A1 | 2/2007 | | |
| EP | 1411879 B1 | 9/2008 | | |
| WO | WO 2012/120036 A1 | 9/2012 | | |

OTHER PUBLICATIONS

Zempleni, Janos, and Donald M Mock. "Biotin biochemistry and human requirements." The Journal of nutritional biochemistry 10.3 (1999): 128-138.*

* cited by examiner

*Primary Examiner* — Bethany Barham
*Assistant Examiner* — Peter Anthopolos

(57) ABSTRACT

Compositions for increasing the rate of metabolism of alcohol in a human and preventing the symptoms of a hangover comprising amino acids of one or both of L-arginine or L-citrulline; one or more of L-glutamine, L-glutamic acid, L-glutamine or theanine; and one or both of L-tyrosine or L-phenylalanine. The compositions may also contain other ingredients, such as B vitamins and plant extracts.

1 Claim, No Drawings

COMPOSITION AND METHOD FOR INCREASING THE RATE OF ALCOHOL METABOLISM AND PREVENTING HANGOVER SYMPTOMS

FIELD OF THE INVENTION

The invention relates to a composition and method that may be used to increase the rate of alcohol metabolism and prevent hangover symptoms.

BACKGROUND

The adverse effects of alcohol consumption are dependent on the amount and rate of consumption as well as genetic and physiological conditions that vary between individuals. The symptoms of a hangover are the delayed indications of the physiological effects of excessive alcohol consumption and can include headaches, sensitivity to sound and light, fatigue, and nausea.

The physiological effects of alcohol consumption include vasodilation (followed later by vasoconstriction), decreased blood oxygen concentration, increased oxygen demand, imbalanced internal pH level, increased carbon dioxide concentration, dehydration, loss of electrolytes, inhibited enzymatic and metabolic activities, excess energy transfer molecules, particularly NADH and ATP, and accumulation of toxic metabolic by-products, particularly Acetaldehyde and its adducts.

Ingested alcohol is absorbed into the blood stream by the stomach and the small intestines. Once in the circulatory system, alcohol triggers the movement of water and electrolytes across the vascular cell membranes into the bloodstream. The movement of electrolytes, especially calcium, out of vascular cells interferes with the myogenic control of blood vessel diameter. The movement of excess water into the bloodstream creates a condition of low blood electrolyte concentration that triggers the release of antidiuretic hormone, also called vasopressin. Vasopressin would normally have a constrictive effect on the blood vessels, but this effect is inhibited by the conditions created by alcohol and its metabolic by-products. The result is dilated blood vessels and a net loss of fluid and electrolytes.

The release of vasopressin continues as long as the concentration of electrolytes remains low and the inhibitory signal is absent. The result is an accumulation of vasopressin that leads to over constriction of blood vessels when the concentrations of alcohol and its metabolic by-products eventually fall. The severity of the constrictive effect of accumulated vasopressin on the diameter of blood vessels varies with location, the concentration of free calcium ions, and the time period of alcohol consumption. Cerebral and coronary arteries are especially vulnerable to excessive vasoconstriction which is also affected by pH levels and carbon dioxide and oxygen concentrations.

Four main enzymes are involved in the metabolism of ethanol: Alcohol Dehydrogenase ("ADH"), Acetaldehyde Dehydrogenase ("ALDH"), Cytochrome P450 ("CYP2E1"), and Catalase.

In most people, the majority of ingested alcohol is metabolized in the liver by ADH into acetaldehyde, a highly reactive by-product that is 20 to 30 times more toxic than alcohol. Acetaldehyde is further metabolized in the mitochondria into acetic acid by ALDH. Acetic acid readily converts to acetate, when the pH is above 5.5. Continuous mitochondrial oxidation of acetaldehyde into acetic acid leads to a build up of acetates and, consequently, to excess acetaldehyde that crosses mitochondrial and cell membranes into the blood stream.

Acetaldehyde has the capacity to form adducts with amino acids, proteins, nucleic acids, enzymes, co-enzymes, and other biomolecules and hinder their activity. Among the most susceptible proteins are hemoglobin and cytochromes, both of which are critically important in the metabolism of alcohol, sugar, proteins, and fats. Acetaldehyde-hemoglobin adducts reduce the affinity of oxygen to hemoglobin, resulting in a decreased oxygen loading. Further, alkaline conditions created by alcohol metabolism increase the affinity of oxygen to free hemoglobin, thereby decreasing the unloading of oxygen. The decreased availability of oxygen leads to the downregulation of the electron transport chain.

During alcohol metabolism there is an increased demand for oxygen. In addition, when the concentrations of alcohol or its by-products are high, Kupffer cells become activated. Their activation releases stimulatory molecules that increase the metabolic activity of hepatocytes. As a result, oxygen demand by cells increases even further and hypoxia and cell death are increased.

Alcohol consumption also leads to the inhibition of carbon dioxide binding to hemoglobin, which downregulates its elimination and leads to increased carbon dioxide concentrations. Excess carbon dioxide reacts with water to produce carbonic acid and hydrogen ions, thereby contributing to a decrease in pH and a risk of carbonic acidosis.

As acetaldehyde continues to accumulate it is converted to acetyl-CoA. Excess acetyl-CoA contributes to a drop in cellular pH by being converted into ketones and contributing to the accumulation of acetic acid and pyruvate, which is converted to lactic acid.

The oxidation of alcohol and acetaldehyde by ADH and ALDH produces an excess of NADH molecules while depleting $NAD^+$. This decreases the ratio of $NAD^+/NADH$, thereby reducing the redox potential of hepatic cells. Excess NADH also contributes to the inhibition of both the citric acid cycle (the "Kreb cycle") and the urea cycle. The downregulation of the Kreb cycle results in an increase in the concentration of acetyl-CoA and subsequent downregulation of the enzyme pyruvate dehydrogenase. The electron transport chain ("ETC") helps decrease the concentration of NADH by the production of ATP and water. The normal functioning of the ETC relies on the availability of oxygen. Both a decrease in oxygen concentration and an increase in ATP concentration can magnify the accumulation of NADH and consequently limit the metabolism of alcohol.

Alcohol metabolism shows steady state kinetics. Increased concentrations of alcohol have little or no effect on the reaction rate of alcohol metabolism. Therefore, the conversion of alcohol to acetaldehyde is not the limiting step in alcohol metabolism. The steady state kinetics of alcohol metabolism is a natural protective mechanism of the body, concerned with limiting the physiological effects of acetaldehyde and its by-products during alcohol metabolism. The composition of the present invention functions to eliminate the by-products of alcohol metabolism, rather than to stimulate the activity of ADH or ALDH.

SUMMARY OF THE INVENTION

One aspect of the present invention is a composition for increasing the rate of the metabolism of alcohol and preventing the symptoms of a hangover, by upregulating anabolic and catabolic reactions involved in eliminating the by-products of alcohol metabolism, thereby limiting and counteracting the physiological effects of alcohol consumption.

One embodiment of the composition according to the present invention contains a preferred combination of amino acids, to upregulate anabolic and catabolic reactions involved in eliminating the by-products of alcohol metabolism.

Another embodiment of the composition according to the present invention contains buffers and, optionally, electrolytes to counterbalance the adverse physiological effects of alcohol metabolism on pH.

Another embodiment of the composition according to the present invention contains compounds, such as arginine, that contribute to the prevention or reduction of excessive vascular constriction, caused by the accumulation of excessive concentrations of vasopressin, and to the maintenance of prolonged vascular dilation.

Another embodiment of the composition according to the present invention contains metabolic stimulators, such as arginine and tyrosine, to enhance the cycling of $NAD^+$ through the stimulation of certain anabolic reactions that require ATP for their metabolism to allow the Kreb cycle to proceed.

Another embodiment of the composition according to the present invention contributes to enhanced oxygen availability and affinity to hemoglobin as well as reduced carbon dioxide concentrations.

The amino acids contained in the composition according to the present invention are specifically chosen so as not to interfere with each other with respect to absorption or function and because they are less likely to contribute to acetyl-CoA accumulation. Certain vitamins, minerals and other compounds that enhance or complement the activity of the amino acids may also be included in the composition.

Another aspect of the present invention is a method of increasing the rate of metabolism of alcohol in a human by upregulating anabolic and catabolic reactions involved in eliminating the by-products of alcohol metabolism.

Another aspect of the present invention is a method of increasing the rate of metabolism of alcohol in a human and preventing the symptoms of a hangover by upregulating anabolic and catabolic reactions involved in eliminating the by-products of alcohol metabolism and reducing vascular constriction caused by the accumulation of vasopressin.

The compositions and methods according to the present invention are described in greater detail, in terms of the following preferred embodiments and examples.

DESCRIPTION OF THE EMBODIMENTS

The composition according to the present invention increases the rate of the metabolism of alcohol by upregulating anabolic and catabolic reactions involved in the elimination of the by-products of alcohol metabolism, rather than stimulating the activity of ADH or ALDH. The composition also prevents the symptoms of a hangover by reducing vascular constriction caused by the accumulation of vasopressin. In particular, the composition upregulates the Kreb cycle, which allows more acetyl-CoA, a by-product of alcohol metabolism, to be eliminated by entering the Kreb cycle. The urea cycle is also upregulated, which converts ATP to ADP and AMP, thereby increasing the demand for ATP from other metabolic reactions. The biosynthesis of creatine and phosphocreatine, the production of human growth hormone, and the production of dopamine are also upregulated, which all contribute to increasing the energy demand.

The composition may also contain buffers and, optionally, electrolytes to counterbalance the adverse physiological effects of alcohol metabolism on pH. Preferably, compounds are included in the composition, such as arginine, that contribute to the prevention or reduction of excessive vascular constriction, caused by the accumulation of vasopressin, and to the maintenance of prolonged vascular dilation. The composition thereby limits and counteracts the physiological effects of alcohol consumption and prevents the symptoms of a hangover.

The composition contains a mixture of amino acids, selected based on their metabolic effects and interaction with one another. The list of amino acids suitable for inclusion in the composition of the present invention, was devised on the basis of the following conditions:

a. Amino acids that are metabolized into acetyl-CoA, either directly or through conversion first to acetoacetyl-CoA and then to acetyl-CoA were not included for their potential to contribute to an excess build-up of acetyl-CoA and thereby decrease the probability of alcohol-derived acetyl-CoA entering the Kreb cycle, including alanine, tryptophan, cysteine, serine, glycine, leucine, isoleucine, and lysine. Tyrosine and phenylalanine were none the less suitable for inclusion because they have an alternate metabolic fate that can be followed when acetyl-CoA or acetoacetyl-CoA are in excess;

b. Amino acids that are metabolized into succinyl-CoA were not included because succinyl-CoA is an inhibitor and rate limiter of the Kreb cycle, including isoleucine, valine, methionine, and threonine;

c. Amino acids that compete for intestinal absorption were limited; and d. Amino acids that are converted into similar metabolic intermediates or products were not included to avoid contributing to reaction inhibition by the accumulation of excess metabolic by-products.

In addition to the above conditions, the amino acids included in the composition of the present invention were preferred over other amino acids that met the above conditions, due to the following desirable chemical and metabolic characteristics:

e. Arginine and glutamine are converted to glutamate before entering the Kreb cycle, where they are converted to alpha-ketoglutarate;

f. Arginine has a positive effect on the release of human growth hormone, which results in higher energy demands;

g. Arginine triggers the biosynthesis of creatine and phosphocreatine, which stores energy in the form of phosphocreatine, thereby increasing the ADP/ATP ratio and allowing the Kreb cycle to proceed;

h. Arginine is a precursor for nitric oxide, which is a powerful vasodilator that helps counteract the effect of high concentrations of vasopressin;

i. Glutamate is an essential reactant of the urea cycle, which consumes ATP and converts $NAD^+$ to NADH;

j. Glutamine improves the intestinal absorption of arginine; and k. Tyrosine is converted to dopamine, which helps stimulate metabolism and the conversion of ATP to ADP.

A preferred embodiment of the composition, according to the present invention, comprises: one or both of L-arginine or L-citrulline; one or more of L-glutamine, L-glutamic acid, L-glutamate, or theanine; and one or both of L-tyrosine or L-phenylalanine.

Another preferred embodiment of the composition comprises: one or both of L-arginine or L-citrulline; one or more of L-glutamine, L-glutamic acid, L-glutamate, or theanine; one or both of L-tyrosine or L-phenylalanine; and one or more of vitamins B1 (thiamine), B2 (riboflavin), B3 (niacin), B5 (pantothenic acid), B6 (pyridoxine), B7 (biotin), B9 (folic acid), B12 (cobalmin), choline, inositol, PABA (para-aminobenzoic acid), ginseng root extract, sodium, chloride, potassium, sugar substitute, calcium, magnesium, zinc, iron, manganese, phosphorus, vitamin D, or vitamin C.

Another preferred embodiment of the composition comprises: L-arginine, L-glutamic acid, L-tyrosine, L-phenylalanine, vitamin B1 (thiamine), vitamin B2 (riboflavin), vitamin B3 (niacin), vitamin B5 (pantothenic acid), vitamin B6 (pyridoxine), vitamin B7 (biotin), vitamin B9 (folic acid), vitamin B12 (cobalmin), choline, inositol, PABA (para-aminobenzoic acid), ginseng root extract, sodium, chloride, potassium, sugar substitute, calcium, magnesium, zinc, iron, manganese, phosphorus, vitamin D, and vitamin C.

The additional vitamins, minerals and other compounds included in this preferred embodiment of the composition function by enhancing or complementing the activity of the amino acids of the composition. For example, buffers and electrolytes may be included in the composition to counterbalance the adverse physiological effects of alcohol metabolism on pH and electrolyte levels.

The composition can be taken by way of oral dosage in the form of pills or beverages, or by injection. Preferably, the composition is taken within 60 minutes following the end of alcohol ingestion.

EXAMPLE 1

In another preferred embodiment of the composition, the composition comprises the following compounds, in the ranges of amount of compound per hundred grams of composition, listed in the table below:

TABLE 1

Ranges of amount per 100 g of composition of compounds in a preferred embodiment of the composition according to the present invention

| Compound | Min/max in 100 g of composition |
| --- | --- |
| B1 Thiamine | 100 mg/900 mg |
| B2 Riboflavin | 100 mg/900 mg |
| B3 Niacin | 100 mg/1200 mg |
| B5 Pantothenic Acid | 200 mg/3000 mg |
| B6 Pyridoxine | 100 mg/900 mg |
| B12 Cobalmin | 300 mcg/3000 mcg |
| B7 Biotin | 300 mcg/3000 mcg |
| B9 Folic Acid | 1300 mcg/13000 mcg |
| Choline | 350 mg/3500 mg |
| Inositol | 100 mg/1100 mg |
| PABA | 2.5 mg/30 mg |
| Ginseng Extract | 4 g/25 g |
| Mn | 0.2 mg/3 mg |
| Ca | 1 g/20 g |
| Vit D | 4000 IU/60000 IU (100 mcg/1,500 mcg) |
| Mg | 250 mg/3000 mg |
| Zn | 10 mg/120 mg |
| Fe | 10 mg/200 mg |
| P | 200 mg/2500 mg |
| Sea Salt | 5 g/12 g |

TABLE 1-continued

Ranges of amount per 100 g of composition of compounds in a preferred embodiment of the composition according to the present invention

| Compound | Min/max in 100 g of composition |
| --- | --- |
| Splenda | 10 tbs/20 tbs (1 g/2 g) |
| Vit C | 1 g/10 g |
| K | 200 mg/2000 mg |
| Arg | 10 g/60 g |
| Glu | 2 g/20 g |
| Tyr | 3 g/30 g |
| Phe | 3 g/30 g |

According to a second aspect of the present invention, a method of increasing the rate of metabolism of alcohol in a human comprises the steps of upregulating anabolic and catabolic reactions involved in eliminating the by-products of alcohol metabolism.

Preferably, the anabolic and catabolic reactions are upregulated by oral administration of the composition described in Example 1, above, within 60 minutes following the end of alcohol ingestion. This affects various anabolic and catabolic reactions, including the Kreb cycle, the urea cycle, biosynthesis of creatine and phosphocreatine, production of human growth hormone, and production of dopamine. Upregulation of the Kreb cycle allows more acetyl-CoA from alcohol metabolism to be eliminated by entering the Kreb cycle, thereby increasing the rate of metabolism of alcohol. Upregulation of the urea cycle consumes ATP and converts $NAD^+$ to NADH. Upregulation of the biosynthesis of creatine and phosphocreatine, production of human growth hormone, and production of dopamine all contribute to increasing the energy demand.

According to a third aspect of the present invention, a method of increasing the rate of metabolism of alcohol in a human and preventing the symptoms of a hangover comprises the steps of upregulating anabolic and catabolic reactions involved in eliminating the by-products of alcohol metabolism and reducing vascular constriction caused by the accumulation of vasopressin.

Preferably, the anabolic and catabolic reactions are upregulated as described above and the vascular constriction is reduced by stimulating production of vasodilators. The vasodilators include nitric oxide, which is produced from arginine.

What is claimed is:

1. A composition for increasing the rate of metabolism of alcohol in a human, comprising:
   L-arginine in amounts ranging from 10 g to 60 g in 100 g of composition;
   L-glutamic acid in amounts ranging from 2 g to 20 g in 100 g of composition;
   L-tyrosine in amounts ranging from 3 g to 30 g in 100 g of composition;
   L-phenylalanine in amounts ranging from 3 g to 30 g in 100 g of composition;
   vitamin B1 (thiamine) in amounts ranging from 100 mg to 900 mg in 100 g of composition;
   vitamin B2 (riboflavin) in amounts ranging from 100 mg to 900 mg in 100 g of composition;
   vitamin B3 (niacin) in amounts ranging from 100 mg to 1200 mg in 100 g of composition;
   vitamin B5 (pantothenic acid) in amounts ranging from 200 mg to 3,000 mg in 100 g of composition;

vitamin B6 (pyridoxine) in amounts ranging from 100 mg to 900 mg in 100 g of composition;
vitamin B7 (biotin) in amounts ranging from 300 mcg to 3,000 mcg in 100 g of composition;
vitamin B9 (folic acid) in amounts ranging from 1,300 mcg to 13,000 mcg in 100 g of composition;
vitamin B12 (cobalmin) in amounts ranging from 300 mcg to 3,000 mcg in 100 g of composition;
choline in amounts ranging from 350 mg to 3,500 mg in 100 g of composition;
inositol in amounts ranging from 100 mg to 1,100 mg in 100 g of composition;
PABA (para-aminobenzoic acid) in amounts ranging from 2.5 mg to 30 mg in 100 g of composition;
ginseng root extract in amounts ranging from 4 g to 25 g in 100 g of composition;
sodium in amounts ranging from 2 g to 5 g in 100 g of composition;
chloride in amounts ranging from 3 g to 7 g in 100 g of composition;
potassium in amounts ranging from 200 mg to 2,000 mg in 100 g of composition;
calcium in amounts ranging from 1 g to 20 g in 100 g of composition;
magnesium in amounts ranging from 250 mg to 3,000 mg in 100 g of composition;
zinc in amounts ranging from 10 mg to 120 mg in 100 g of composition;
iron in amounts ranging from 10 mg to 200 mg in 100 g of composition;
manganese in amounts ranging from 0.2 mg to 3 mg in 100 g of composition;
phosphorus in amounts ranging from 200 mg to 2,500 mg in 100 g of composition;
vitamin D in amounts ranging from 100 mcg to 1,500 mcg in 100 g of composition; and
vitamin C in amounts ranging from 1 g to 10 g in 100 g of composition.

* * * * *